US008515508B2

(12) United States Patent
Kawamura et al.

(10) Patent No.: US 8,515,508 B2
(45) Date of Patent: Aug. 20, 2013

(54) METHOD FOR MEASURING A CONCENTRATION OF A BIOGENIC SUBSTANCE CONTAINED IN A LIVING BODY

(75) Inventors: Tatsurou Kawamura, Kyoto (JP); Masahiko Shioi, Osaka (JP); Masaru Minamiguchi, Kyoto (JP)

(73) Assignee: Panasonic Corporation, Osaka (JP)

(*) Notice: Subject to any disclaimer, the term of this patent is extended or adjusted under 35 U.S.C. 154(b) by 40 days.

(21) Appl. No.: 13/267,625

(22) Filed: Oct. 6, 2011

(65) Prior Publication Data
US 2012/0029326 A1 Feb. 2, 2012

Related U.S. Application Data (63) Continuation of application No. PCT/JP2011/000984, filed on Feb. 22, 2011.

(30) Foreign Application Priority Data

Apr. 20, 2010 (JP) ................................. 2010-096793

(51) Int. Cl.
*A61B 5/1455* (2006.01)
(52) U.S. Cl.
USPC .......................................... 600/316; 600/310
(58) Field of Classification Search
USPC .................................................. 600/309–344
See application file for complete search history.

(56) References Cited

U.S. PATENT DOCUMENTS

| 6,485,703 | B1 | 11/2002 | Cote et al. |
| 2002/0058863 | A1 | 5/2002 | Petersson et al. |
| 2004/0036854 | A1 | 2/2004 | Fukuda et al. |
| 2005/0079630 | A1 | 4/2005 | Lazarenko-Manevich et al. |
| 2007/0139646 | A1 | 6/2007 | Singh |
| 2009/0118605 | A1 | 5/2009 | Van Duyne et al. |
| 2009/0233810 | A1 | 9/2009 | Hwang et al. |
| 2010/0195106 | A1 | 8/2010 | Ogawa |

FOREIGN PATENT DOCUMENTS

| JP | 2001-027636 | 1/2001 |
| JP | 2004-510527 | 4/2004 |
| JP | 2005-258364 | 9/2005 |
| JP | 2007-248284 | 9/2007 |
| JP | 2008-301944 | 12/2008 |
| WO | WO 2007/108453 A1 | 9/2007 |

OTHER PUBLICATIONS

Melissa F. Mrozek et al., "Detection and Identification of Aqueous Saccharides by Using Surface enhanced Raman Spectroscopy," Analytical Chemistry, vol. 74, No. 16, 4609-4075, 2002.

(Continued)

*Primary Examiner* — Eric Winakur
*Assistant Examiner* — Marjan Fardanesh
(74) *Attorney, Agent, or Firm* — McDermott Will & Emery LLP (57) ABSTRACT The object of the present invention is to provide a method for measuring concentration of a biological substance contained in a living body in which deterioration of the accuracy due to the reflected light and the interruption component is suppressed. Linear-polarized light is emitted to a particle chip implanted in the skin with modulating its modulating direction continuously. A surface enhanced Raman scattering light of the biological substance generated on the particle chip. A concentration of the biological substance is calculated based on the received signal. The receiving signal satisfy the following equation:

$R(t) = Am \cdot \sin(\omega t) + D$, where $R(t)$: received signal, $Am$: amplitude, $t$: time, $D$: a constant number, and $\omega$: angular speed.

12 Claims, 10 Drawing Sheets

(56) References Cited

OTHER PUBLICATIONS

Itoh Tamitake et al., "Polarization dependences of surface Plasmon bands and surface-enhanced Raman bands of single Ag nanoparticles," Applied Physics Letters, American Institute of Physics, Melville, NY, vol. 83, No. 11, Sep. 15, 2003, pp. 2274-2276, XP012035126.

Camargo P.H.C. et al., "Measuring the SERS enhancement factors of dimmers with different structures constructed from silver nanocubes," Chemical Physics Letters, vol. 484, No. 4-6, Jan. 7, 2010, pp. 304-308, XP026817323.

Pedro H.C. Camargo et al., "Measuring the surface-enhanced Raman scattering enhancement factors of hot spots formed between an individual Ag nanowire and a sinlge Ag nanocube," Nanotechnology, vol. 20, No. 43, Oct. 2009, pp. 434020, XP020164924.

Jeremy D. Driskell et al., "Infectious Agent Detection with SERS-Active Silver Nanorod Arrays Prepared by Oblique Angle Deposition," IEEE Sensors Journal, IEEE Service Center, vol. 8, No. 6, Jun. 1, 2008, pp. 863-870, XP011215529.

METHOD FOR MEASURING A CONCENTRATION OF A BIOGENIC SUBSTANCE CONTAINED IN A LIVING BODY

CROSS REFERENCE TO RELATED APPLICATION APPLICATIONS

This is a continuation of PCT International Application PCT/JP2011/000984 filed on Feb. 22, 2011, claiming priority of Japanese Patent Application No. 2010-096793, filed on Apr. 20, 2010, the disclosures of which applications are hereby incorporated by reference.

TECHNICAL FIELD

This invention relates to a method for measuring a concentration of a biogenic substance contained in a living body.

BACKGROUND ART

A concentration of a biogenic substance such as glucose contained in a living body is measured on the basis of reflected light or transmitted light irradiated on the living body.

Patent Document 1 discloses a method for measuring a three-dimensional distribution of a biogenic substance in a living body. According to the method, first, laser lights of various wavelengths are irradiated so that they are focused in the living body. The reflected light is analyzed by spectroscopy while the region where the laser lights are irradiated and the position where the laser lights are focused are scanned by the irradiated lights to measure the three-dimensional distribution.

Patent Document 2 discloses a method for measuring a glucose concentration. According to the method, first, a particle is implanted in the upper layer of a skin. The particle contains a reagent to change a fluorescence property on the reaction with glucose. Next, light of an exciting wavelength is irradiated from the outside of the living body to measure fluorescence generated at the particle through the skin. On the basis of the measured fluorescence, the glucose concentration is measured.

CITATION LIST

Patent Literature

[PTL 1]
Japanese patent laid-open publication No. 2008-301944.
[PTL 2]
Japanese patent laid-open publication No. 2004-510527.
[PTL 3]
International publication No. 2007/108453.
[PTL 4]
Japanese patent laid-open publication No. 2007-248284.

Non Patent Literature

[NPL 1]
Melissa F. Mrozek, and Michael J. Weaver, "Detection and Identification of Aqueous Saccharides by Using Surface enhanced Raman Spectroscopy", Analytical Chemistry, Vol. 74, No. 16, 4069-4075, 2002

SUMMARY OF INVENTION

Technical Problem

However, light irradiated to a living body is reflected strongly to all directions on the surface of a skin. The intensity of the total reflected lights usually is not less than four percent of the intensity of the irradiated light, whereas the intensity of Raman scattering light is merely equal to or less than $10^{-7}$ times of the intensity of the irradiated light.

Namely, the reflected light is much stronger than the Raman scattering light to be detected. Accordingly, when even the slightest reflected light is added to a light sensor, the accuracy is lowered. In other words, the reflected light is stray light, which lowers the accuracy.

The amount of the stray light can be lowered by using a filter through which only the light of a specific wavelength transmits. However, the stray light can't be removed completely.

Furthermore, the surface of a skin has a component (hereinafter, "interruption component") with a spectrum which overlaps absorption spectrum or Raman spectrum of a biogenic substance such as glucose and protein. Since the spectrum amount of the interruption component can't be lowered enough even through the filter, the interruption component also lowers the accuracy.

A light property on the surface of a skin based on the concentrations of a reflectance and the interruption component differs depending on the position to be measured even in an identical living body. Furthermore, the light property changes with time even in the identical position. This means that the accuracy is insufficient even when a method for compensating the influence of the stray light and the interruption component is used.

Not only the light reflected on the surface of the skin but also light diffused or scattered under the skin are stray lights. The stray lights lower the accuracy.

Solution to Problem

The following method solves the above problem(s).

[1] : A method for measuring a concentration of a biological substance contained in a living body with a measurement device, comprising the following steps (A) to (C):

a step (A) of preparing the measurement device comprising
a projection module emitting a linear-polarized light with a wavelength of lambda $_1$,
a filter in which a center wavelength is lambda $_2$, and
a light sensor,
the projection module comprising a polarization modulator which modulates the polarization direction of the linear-polarized light continuously,
a step (B) of emitting the linear-polarized light from projection module to a particle chip implanted in the skin of the living body while continuously modulating the polarization direction of the linear-polarized light by the polarization modulator to receive a surface enhanced Raman scattering light generated on the particle chip as the signal R(t) received by the light sensor through the filter, wherein
the particle chip comprises a plurality of particles with longitudinal axis on the surface thereof,
each of the longitudinal axes of the plurality of particles is oriented in an identical direction, and
the following equations (III) and (VI) are satisfied:
[Math. 3]

$$R(t) = A m \cdot \sin(\omega t) + D \quad \text{(III)}$$

R(t): received signal
Am: amplitude
t: time
D: a constant number
ω: angular speed

[Math. 6]

$$\lambda_2 = \frac{10^7 \cdot \lambda_1}{10^7 - B \cdot \lambda_1} \text{ (nm)} \quad \text{(VI)}$$

B: Raman shift of the biological substance
a step (c) of calculating the concentration of the biological substance from the Am and a standard curve.

[2]: A method of [1], wherein the value of the full width at half maximum of the filter is 3 nm.

[3]: A method of [1], wherein the biological substance is glucose, and the B is 1120 cm$^{-1}$.

[4]: A method of claim 1, wherein the lambda$_1$ is 785 nm and lambda$_2$ is 860.7 nm.

[5]: A method of [3], wherein the lambda$_1$ is 785 nm and lambda$_2$ is 860.7 nm.

[6]: A method of [1], wherein the measurement device comprises a computer,
the computer stores the standard curve, and
the computer calculates the concentration of the biological substance in the step (C).

[7]: A method of [3], wherein the measurement device comprises a computer,
the computer stores the standard curve, and
the computer calculates the concentration of the biological substance in the step (C).

[8]: A method of [4], wherein the measurement device comprises a computer,
the computer stores the standard curve, and
the computer calculates the concentration of the biological substance in the step (C).

[9]: A method of [5], wherein the measurement device comprises a computer,
the computer stores the standard curve, and
the computer calculates the concentration of the biological substance in the step (C).

Advantageous Effects of Invention

The present invention suppresses the deterioration of the accuracy due to the reflected light and the interruption component. Furthermore, the influence of difference depending on the position of the light property of the surface of the skin, and the influence of a chronological change can be avoided.

BRIEF DESCRIPTION OF DRAWINGS

[FIG. 1]
[FIG. 2]
[FIG. 3]
[FIG. 4]
[FIG. 5]
[FIG. 6]
[FIG. 7]
[FIG. 8]
[FIG. 9]
[FIG. 10]
[FIG. 11]
[FIG. 12]

DESCRIPTION OF EMBODIMENTS (Embodiment 1)
A method and a device for measuring a concentration of a biogenic substance according to the embodiment 1 are described with reference to FIG. 1 to FIG. 4.

Figure 1:
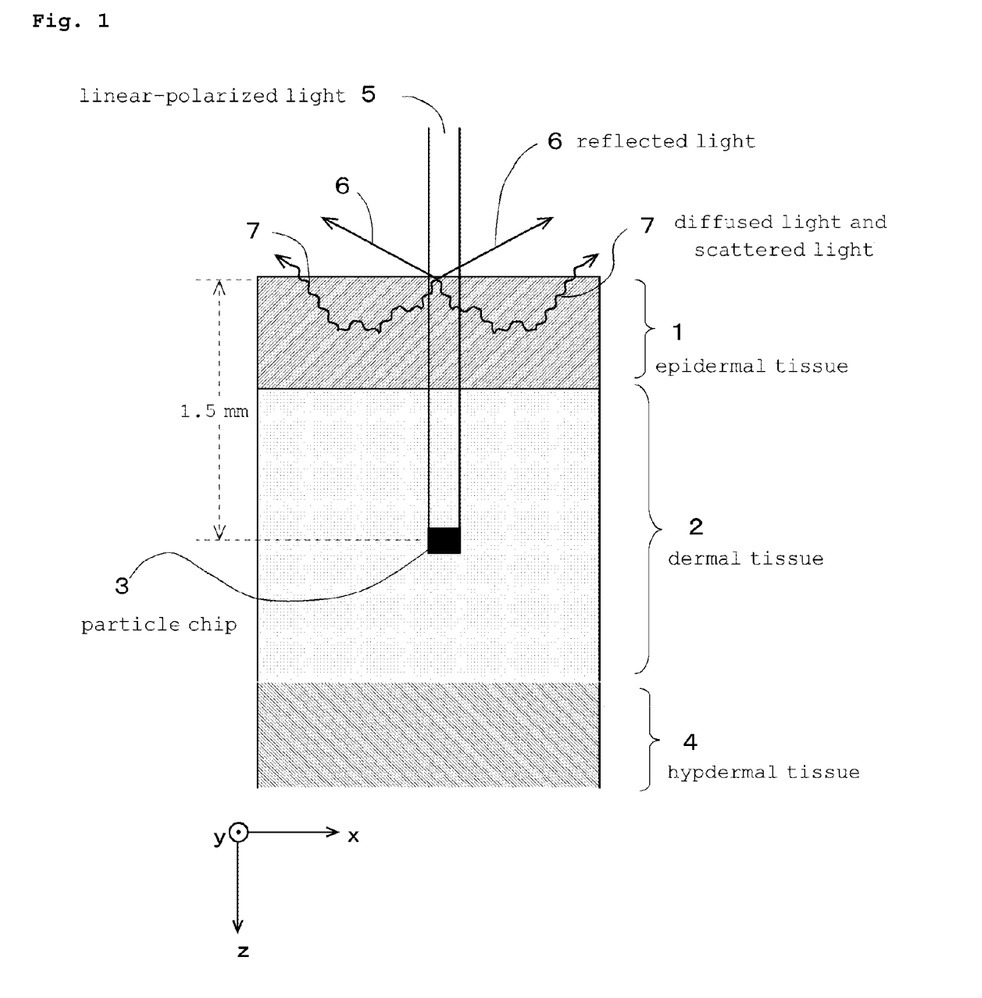
FIG. 1 shows a cross-sectional view of the skin in the embodiment 1.

FIG. 1 shows a cross-sectional view of a skin irradiated by light. An epidermal tissue 1 is located at the surface of the living body. The epidermal tissue 1 has a thickness of approximately 0.2 to 0.5 mm. A dermal tissue 2 has a thickness of approximately 0.5 to 2 mm. A particle chip 3 is implanted in the dermal tissue 2 and maintained to be immersed in an interstitial fluid, which is a living fluid between tissue cells. The term "body fluid" used in the specification means an interstitial fluid.

Because the dermal tissue 2 has a plurality of blood capillaries, the body fluid contains biogenic substances in the blood capillaries. In particular, because glucose has high osmosis, glucose concentration in the body fluid has high correlativity with blood sugar level.

Hypodermal tissue 4 is constituted mainly with adipose tissue. Linear-polarized light 5 has, for example, a wavelength of 785 nm, and a shape of circular beam with a diameter of 100 micro meters. The linear-polarized light 5 penetrates the epidermal tissue 1 to be irradiated on the particle chip 3. The linear-polarized light 5 propagates along z direction shown in FIG. 1. The polarization direction of the linear-polarized light 5 is in the xy plane.

The liner-polarized light 5 is reflected by the surface of the skin to generate reflected light 6. The reflected light 6 includes Raman scattering light and fluorescence of the interruption component. Namely, the reflected light 6 includes not only light having the identical wavelength to the wavelength of the linear-polarized light 5 but also Stokes light component and fluorescence of the Raman Scattering light, which has longer wavelength. The reflected light 6 also includes anti-Stokes light component. The anti-Stokes light component is much weaker than the Stokes light component, and has shorter wavelength than the linear-polarized light 5.

When the liner-polarized light 5 is irradiated, diffused light and scattered light 7 generate is generated in addition to the reflected light 6, because refraction index in the epidermal tissue 1 is nonuniform. The diffused light and scattered light 7 also includes not only light having identical wavelength to the linear-polarized light 5 but also the Raman scattering light and fluorescence of the interruption component, similar to the reflected light 6.

Figure 2:
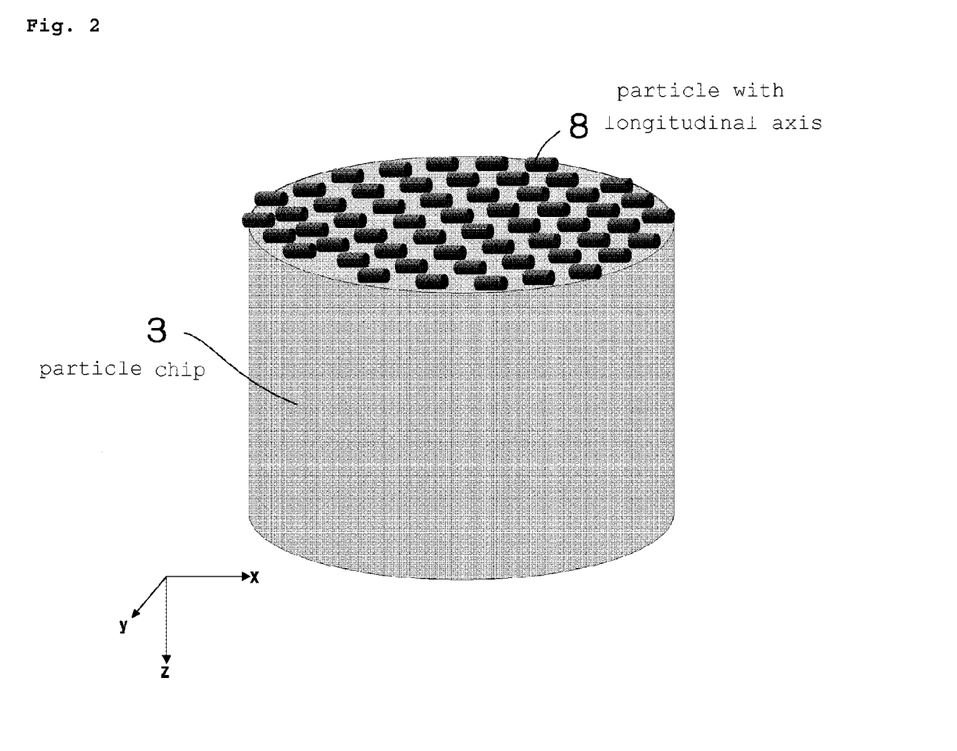
FIG. 2 shows a particle chip 3.
Figure 3:
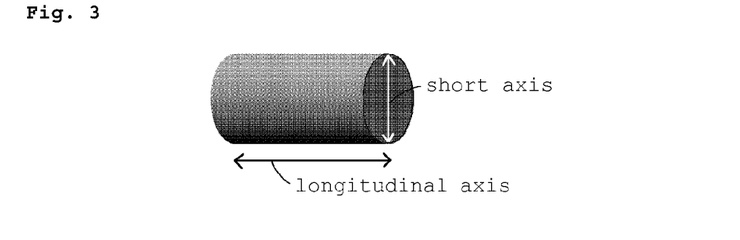
FIG. 3 shows an example of particle with longitudinal axis 8.

FIG. 2 shows a particle chip 3. The particle chip 3 comprises a substrate and particles with longitudinal axis 8 (hereinafter occasionally called simply "particle") disposed on the surface of the substrate. The particles with longitudinal axis 8 generate localized surface Plasmon resonance by irradiating light. One example of the particles with longitudinal axis 8 is gold nano-rod with a diameter of approximately 10 nm and a length of 38 nm. The particles 8 have localized surface Plasmon resonance wavelength of 785 nm.

The substrate has a diameter of approximately 100 micro meters and a thickness of 100 micro meters. An example of the material of the substrate is a resin such as acrylic resin, glass, and silicon. The particles 8 are disposed in such a manner that respective longitudinal axes directions are parallel to x direction. Y direction is orthogonal to the x direction in the surface of the substrate. Z direction is a direction along the thickness of the substrate. WO2007/108453 and Japanese patent laid-open publication No. 2007-248284 disclose the particle chip 3 in more detail.

As shown in FIG. 1, the particle chip 3 is implanted in the dermal tissue 2 so that the plane which comprises the particles 8 is parallel to the epidermal tissue 1. The distance from the epidermal tissue 1 to the particle chip 3 is approximately 1.5 mm.

When the linear-polarized light polarized along x direction is irradiated on the particle chip 3, the localized surface plasmon resonance is generated to increase electromagnetic field strength on the periphery of the particles 8. This causes the Raman scattering light of the biogenic substance located on the periphery (0.5 to 30 nm) of the particles 8 to be increased, too. Thus, surface enhanced Raman scattering light is generated.

An intensity of the surface enhanced Raman scattering light is more than $10^4$ times as that of usual Raman scattering light. Accordingly, the surface enhanced Raman scattering light generated on the periphery of the particles 8 has extremely greater intensity than the Raman scattering light generated in the skin surface, the epidermal tissue 1, or the dermal tissue 2. This means that the Raman scattering light of a biogenic substance contained in a body fluid on the periphery of the particles 8 is selectively increased. Thus, the influence of the stray light and the interruption component is lowered.

The amount of the biogenic substance such as glucose contained in a living body is extremely smaller than the amount of the interruption component contained in the living body. Accordingly, usual Raman scattering light of glucose has extremely smaller intensity than the stray light and the Raman scattering light of the interruption component of the skin surface and the epidermal tissue 1. For this reason, the usual Raman scattering light of glucose may not extracted.

However, the Raman scattering light of glucose contained in a body fluid of the dermal tissue 2 can be increased with the particle chip 3. This allows the Raman scattering light of glucose to be selectively extracted. Because the intensity of the surface enhanced Raman scattering light of glucose is proportional to the concentration of the glucose, the concentration of glucose can be calculated from the intensity of the surface enhanced Raman scattering light of glucose.

Figure 4:
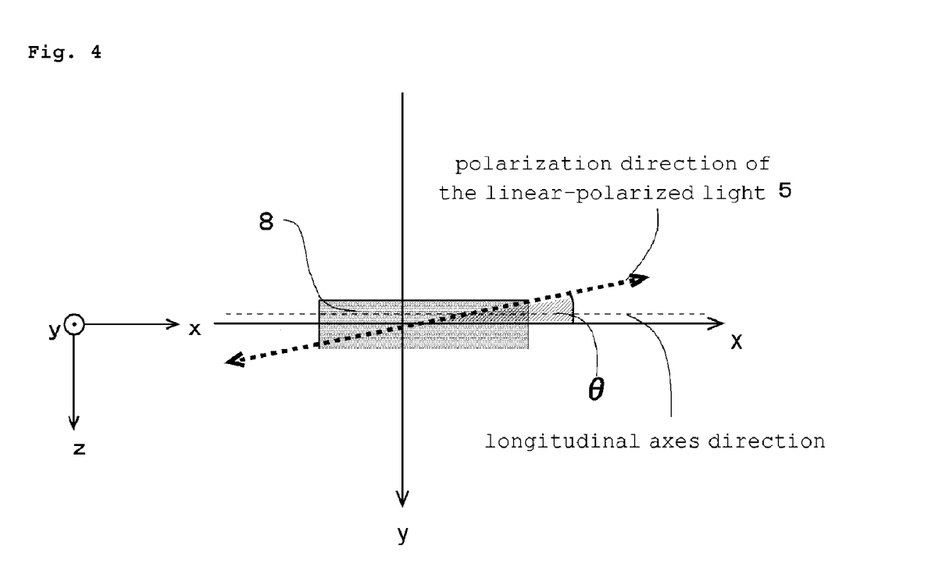
FIG. 4 shows the relationship between the particle 8 and the polarization direction of the light 5.

FIG. 4 shows the relationship between the particles 8 and the polarization direction of the linear-polarized light 5. The dashed line in FIG. 3 indicates the polarization direction. The longitudinal axes of the each particles 8 are parallel to the x direction. The angle between a polarize direction of the linerpolarized light 5 and x direction is theta.

While the linear-polarized light 5 is irradiated along z direction, the polarization direction of the linear-polarized light 5 is modulated. Namely, theta in FIG. 4 varies. A component intensity I, namely power, of the linear-polarized light 5 along x direction varies depending on the variation of theta. The intensity is represented by the following equation (I).

[Math. 1]

$$I = I_0 \times (\cos \theta)^2 \qquad (I)$$

I: component intensity of the linear-polalized light 5 along x direction $I_0$: intensitiy of the linear-polalized light 5 (power)

When theta varies, the component intensity I (power) of the linear-polarized light 5 along x direction may be varied, while the position where the linear-polarized light 5 is irradiated on the skin surface and the intensity of the linear-polarized light 5 are maintained without any change. When the particles 8 are nano-rods, the surface enhanced Raman scattering light represented by the following equation (II) is generated. The intensity S of the surface enhanced Raman scattering light is proportional to the component intensity I.

[Math. 2]

$$S = A \times I = I_0 \times (\cos \theta)^2 \qquad (II)$$

S: the intensity (power) of the surface enhanced Raman scattering light

A: a proportional constant

It is understood from the above formula (II) that the intensity of the surface enhanced Raman scattering light is varied depending on modulation of the polarization direction of the liner-polarized light 5. Accordingly, only the surface enhanced Raman scattering light of the biogenic substance on the periphery of the particles 8 is measured by extracting only the Raman scattering light which varies synchronizing with modulation of the polarization direction of the linear-polarized light 5.

Figure 5:
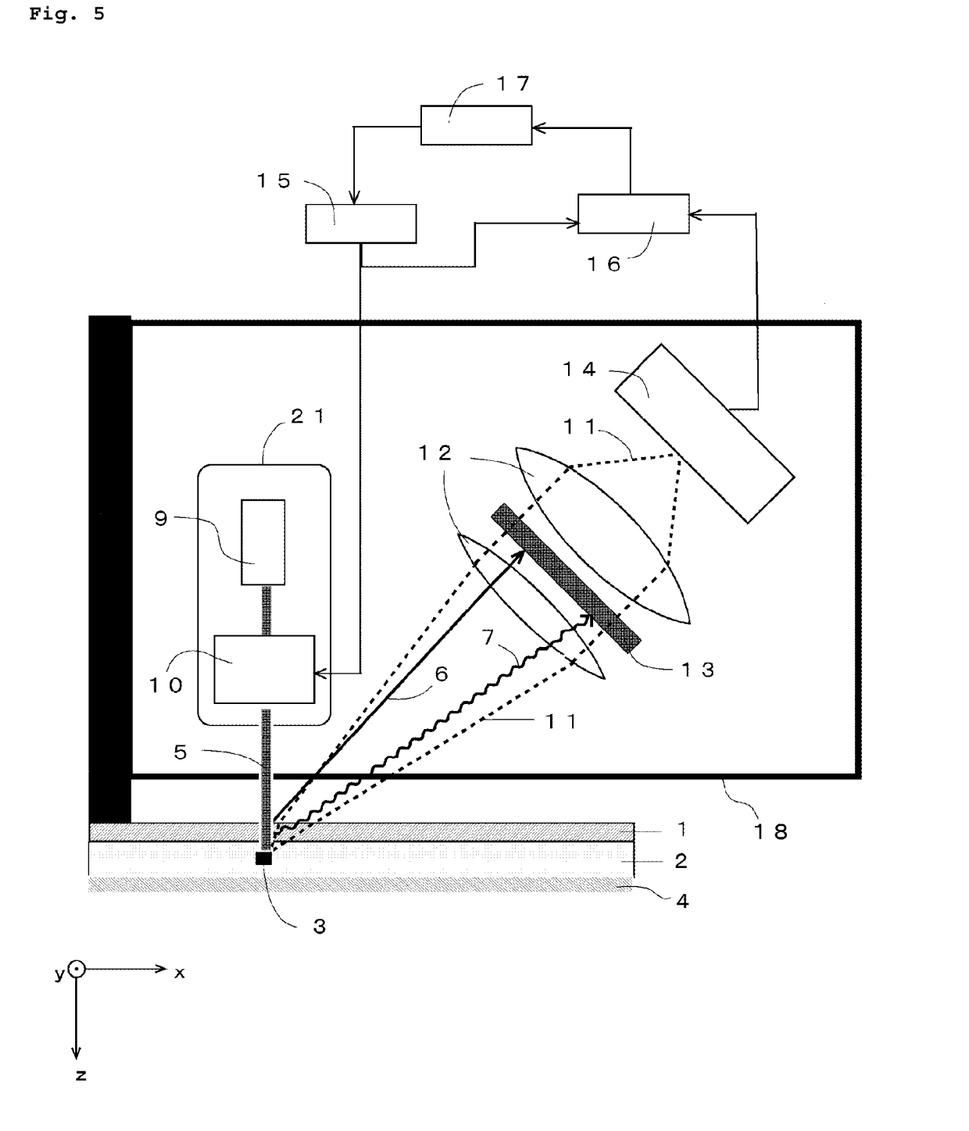
FIG. 5 shows a measuring device according to the embodiment 1.

FIG. 5 shows a measuring device according to the embodiment 1. A projection module 21 modulates the polarization direction of the linear-polarized light 5 while the projection module 21 irradiates the linear-polarized light 5 to the particle chip 3. The projection module 21 comprises a light source 9 comprising a semiconductor laser or an irradiation light system, and a polarization modulator 10 modulating the polarization direction. The semiconductor laser emits linear-polarization light 5 with a wavelength of 785 nm and an intensity of 10 micro watts. The polarization modulator 10 modulates continuously the polarization direction of the linear-polarized light 5, synchronizing with a modulation signal, which is described later.

Figure 12:
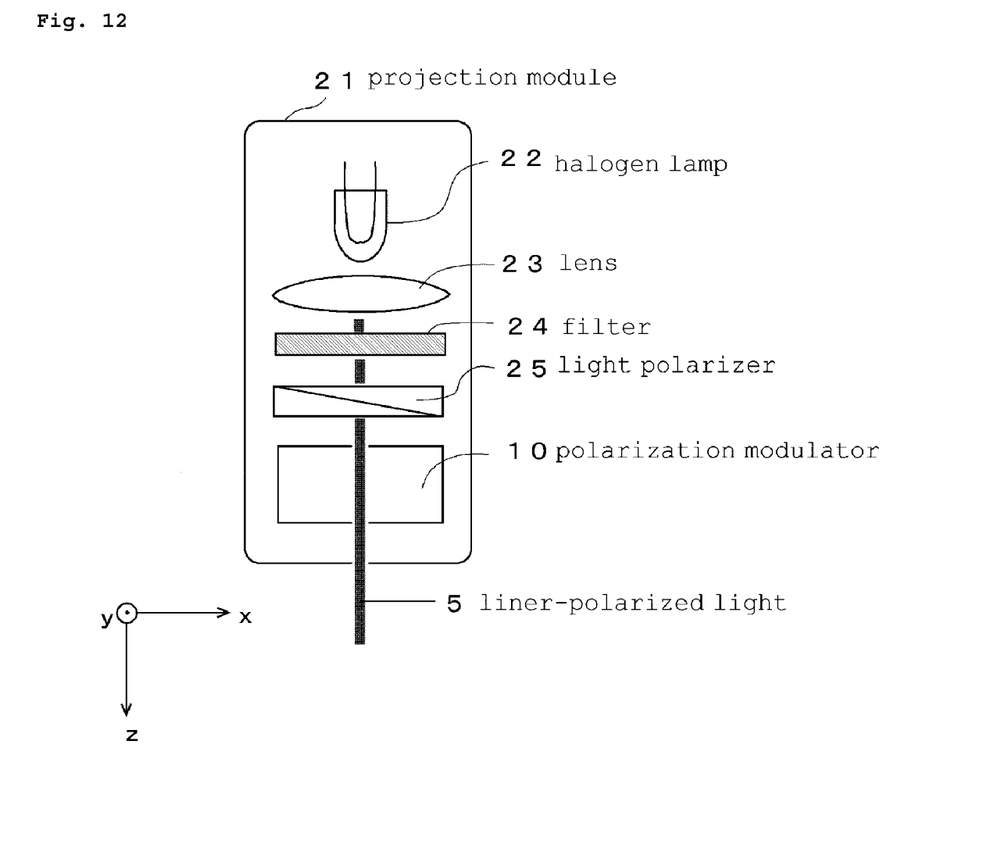
FIG. 12 shows an example of the projection module.

FIG. 12 shows another example of the projection module 21. A halogen lamp 22 emits white light. A lens 23 causes the light which the halogen lamp 22 emits to be parallel light. Light with a wavelength of 785 nm penetrates a filter 24. Only the linear-polarized light included in the light which has penetrated the filter 24 penetrates a light polarizer 25. The polarization modulator 10 modulates continuously the polarization direction of the linear-polarized light which has penetrated through the light polarizer.

As shown in FIG. 5, a surface enhanced Raman scattering light 11 generated in the particle chip 3 is focused on a light sensor 14 through a light system 12. The light system 12 is constituted with a lens group.

Only the light having a specific range of wavelength penetrates filter 13. The wavelength of the light which penetrates the filter 13 agrees with a wavelength of the Raman scattering light of the biological substance.

A signal generator 15 supplies a modulation signal to rotate the polarization direction to the polarization modulator 10. A lock-in amplifier 16 uses the modulation signal as a reference signal to perform phase detection of the output signal from the light sensor 14. A computer 17 calculates a concentration of the biogenic substance on the basis of the output signal of the lock-in amplifier 16 to control the signal generator 15. A support 18 holds the projection module 21, the light system 12, the filter 13, and the light sensor 14.

The polarization modulator 10 modulates continuously the polarization direction of the linear-polarized light 5.

Figure 6:
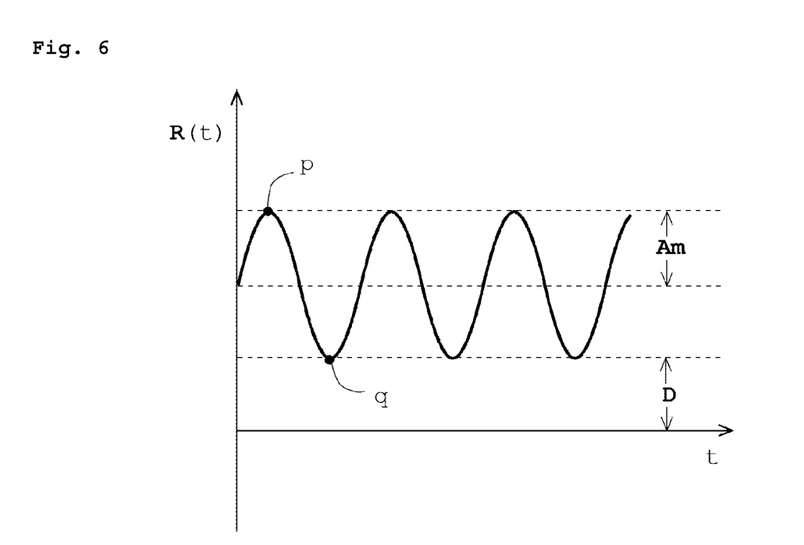
FIG. 6 is a graph showing the relationship between time (t) and the light-receiving signal (R(t)), wherein Am is an amplitude.

FIG. 6 shows the relationship between the time (t) and the surface enhanced Raman scattering light 11, in a case where the linear-polarized light 5 is modulated continuously. The surface enhanced Raman scattering light 11 is measured as the signal received by the light sensor 14. The vertical axis represents the received light R(t). The horizontal axis represents time t. The relationship satisfies the following equation (III):

[Math. 3]

$$R(t) = Am \cdot \sin(\omega t) + D \quad \text{(III)}$$

R(t): received signal
Am: amplitude
t: time
D: a constant number
$\omega$: angular speed An example of the rotation frequency f of the linear-polarized light 5 is 270 Hz. In this example, the relationship is well known between rotation frequency f and angular speed $\omega$ as follows: $f = \omega/2\pi$. Therefore, in this case, $f = \omega/2\pi = 270$ Hz, and angular speed $\omega$ for rotation of the linear-polarized light 55 is represented in the following equation: $\omega = 270 \times 2\pi$(rad/sec). In addition, the equation (III) is applicable for any rotation frequency, for example 270 Hz. The signal R(t) received by the light sensor 14 is represented by a sine wave. At the moment when the signal intensity which is recorded as the upper limit p of the sine wave is detected, the polarization direction of the linear-polarized light 5 is parallel to the x direction (theta is 0 degrees). At the moment when the signal intensity which is recorded as the lower point q of the sine wave is detected, the polarization direction of the linear-polarized light 5 is parallel to the y direction (theta is 90 degrees). The intensity of the surface enhanced Raman scattering light becomes largest at the moment when theta is 0 degrees, and becomes smallest at the moment when theta is 90 degrees because of above equation (II).

An amplitude Am corresponds to the intensity of the surface enhanced Raman scattering light of the biological substance. Namely, the amplitude Am varies proportionally to the intensity of the surface enhanced Raman scattering light.

The D is a component which fails to vary regardless of the situation where the linear-polarized light 5 is irradiated on the particle 3. D represents the intensity of the stray light and the interruption component. D fails to affect the output signal of the lock-in amplifier 16.

The procedure to calculate the concentration of the biological substance from the amplitude Am is described below. In the following description, glucose is exemplified as the biological substance.

FIG. 1 of non-patent document 1 shows the surface enhanced Raman scattering light of glucose. The surface enhanced Raman scattering light of glucose has a plurality of peaks specific to glucose in the Raman shift range of 1000 to 1500 $cm^{-1}$.

Of the plurality of peaks, the peak with a Raman shift of 1120 $cm^{-1}$ fails to overlap the peaks of the Raman scattering light spectra of albumin and creatinine. Accordingly, the intensity of the surface enhanced Raman scattering light with the Raman shift of 1120 $cm^{-1}$ is proportional only to the concentration of glucose.

When the wavelength of the linear-polarized light 5 from the projection module 21 is 785 nm, a filter through which light having wavelength of 860.7 nm can pass is used as the filter 13. The reason thereof is described below.

The relationship between wavelength lambda and wave number k satisfies the following equation (IV):

[Math. 4]

$$k(\text{cm}^{-1}) = \frac{10^7}{\lambda} \text{ (nm)} \quad \text{(IV)}$$

The wavelength of 785 nm is 12739 $cm^{-1}$ in wave number. Accordingly, the Raman scattering light specific to glucose (Raman shift is 1120 $cm^{-1}$) is calculated by the following equation. $12739(\text{cm}^{-1}) - 1120(\text{cm}^{-1}) = 11619(\text{cm}^{-1})$ It is converted into wavelength of 860.7 nm by the equation (IV).

For example, a filter with the central wavelength of 860.7 nm and the value of the full width at half maximum is 3 nm can be used as the filter 13. The penetration range of the filter is 859.2 to 862.2 nm.

The penetration range is from 11599 to 11639 $cm^{-1}$ in wave number. Namely, the filter 13 penetrates only the Raman scattered light with Raman shift from 1100 to 1140 $cm^{-1}$ ((11619−20) to (11619+20)$cm^{-1}$) selectively, but does not penetrate reflected light 6 and Raman scattered light of interruption component. If the intensity of the linear-polarized light 5 is enhanced in order to enhance the intensity of the surface enhanced Raman scattered light, the intensity of the reflected light 6 and the Raman scattered light of interruption components is also enhanced. However, according to the device for measuring of the embodiment 1, reflected light 6 and the Raman scattered light of the interruption components are shielded by the filter 13, and do not achieve to the light sensor 14. Thus, only the signal R(t) specific to the target substance can be measured with enough intensity.

The center wavelength lambda$_2$ of the filter which is used for measuring a glucose concentration as the filter 13 is calculated by the following formula (V). Lambda represents a wavelength of the linear-polarization light 5 emitted by the projection module 21.

[Math. 5]

$$\lambda_2 = \frac{10^7 \cdot \lambda_1}{10^7 - 1120 \cdot \lambda_1} \text{ (nm)} \quad \text{(V)}$$

$\lambda_2$: the center wavelength of the filter 13
$\lambda_1$: the wavelength of the linear-polarized light 5

Figure 11:
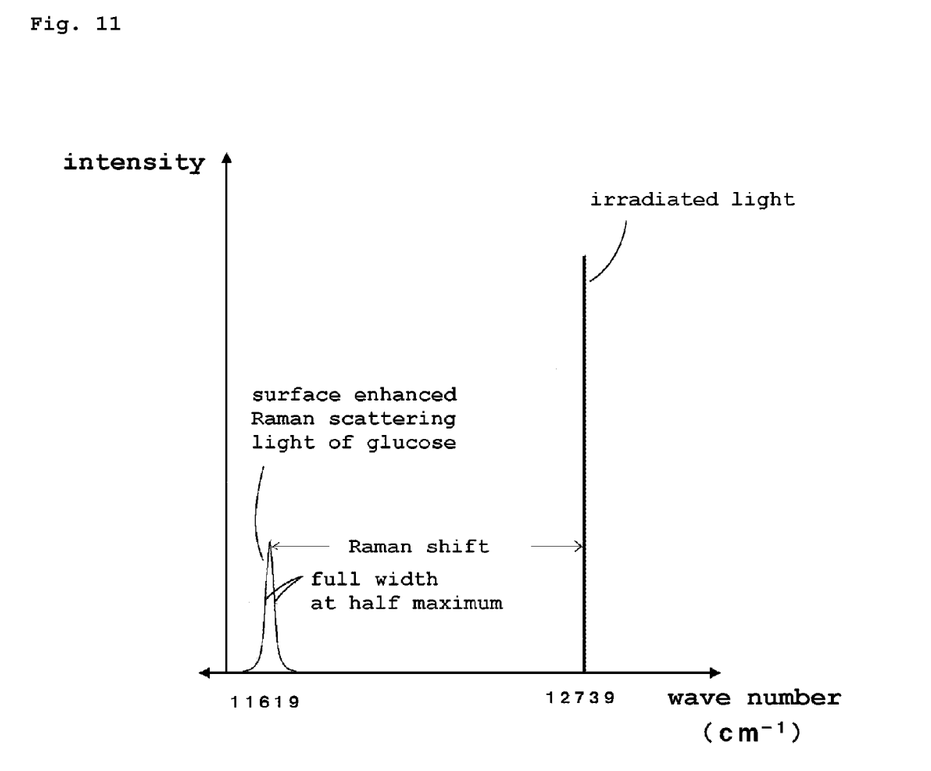
FIG. 11 shows surface enhanced Raman scattering light.

The graph shown in FIG. 11 shows the relationship of the irradiated light, the surface enhanced Raman scattering light, the Raman shift, and the value of the full width at half maximum.

The wavelength and the width thereof of the surface enhanced Raman scattering light specific to glucose agree with the wavelength and the width of the penetration spectrum of the filter 13, respectively, because the surface enhanced Raman scattering light specific to glucose penetrates the filter 13, however, other light fails to penetrate the filter 13.

As described above, the surface enhanced Raman scattering light of glucose with the Raman shift of 1120 cm$^{-1}$ is measured selectively with the measuring device according to the embodiment 1. The intensity of the surface enhanced Raman scattering light is proportional to the amplitude Am.

Separately of determining the amplitude Am, the concentration of glucose contained in a blood of a fasting living body (blood sugar level) is measured by use of a typical blood sugar meter. Simultaneously, the amplitude Am is measured with the measuring device according to the embodiment 1.

Figure 10:
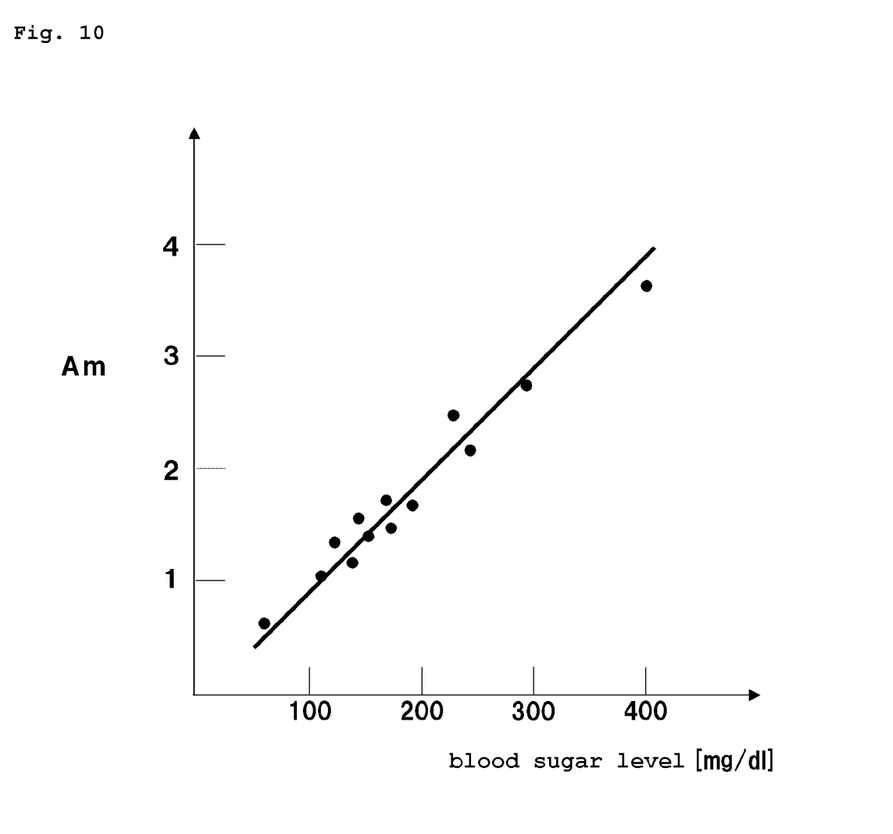
FIG. 10 shows an example for preparing a standard curve.

An Example for preparation of a standard curve is shown in below. Ten minutes later taking predetermined amount of glucose, a blood sugar level of an examinee is measured by use of a conventional method. In parallel, the surface enhanced Raman scattering light generated on the particle chip 3 is measured with use of the measuring device according to the embodiment 1. Thus, amplitude Am is obtained. This is repeated for two hours every 10 minutes to obtain thirteen data sets of the blood sugar level and the amplitude Am. From the data sets, a standard curve between the blood sugar level and the amplitude Am is prepared.

FIG. 10 shows an example of the graph of the standard curve. The vertical axis represents the amplitude Am. The horizontal axis represents the blood sugar level. The thirteen data sets are plotted on the graph to prepare a line which approaches these as the standard curve. Based on the standard curve, the blood sugar level is calculated from the amplitude Am. Needless to say, the number of data sets is not limited to thirteen. The standard curve may be prepared from at least two data sets.

The blood sugar level of the healthy human varies in the range of 70 to 160 mg/dl. The blood sugar level of patients affected with diabetes varies in the range of 70 to 500 mg/dl.

Because the skin of each individual has different propagation properties of light, preferably, a standard curve is prepared for each individual. Because the difference of the implantation position also causes the propagation properties of light to differ, a standard curve is preferably prepared whenever the particle chip 3 is implanted into the skin. This allows the blood sugar level to be measured with high accuracy.

The method and the device for measuring a concentration of a biological substance according to the embodiment 1 is unaffected by the reflected light on the skin surface and the interruption components.

In the embodiment 1, the light with a wavelength specific to the biological substance from the surface enhanced Raman scattering light of the biological substance is extracted with the filter 13. Instead of the filter 13, a spectral apparatus may be provided in the light sensor 14 to detect a spectrum of the surface enhanced Raman scattering light. A signal of the light with the wavelength specific to the biological component can be extracted.

Instead of gold nano-rods, a particle in which the surface of a dielectric material composed of silica is coated by a metal such as gold or silver may be used.

In the embodiment 1, the irradiation light which is emitted by the projection module 21 has a wavelength of 785 nm, which has the following advantages.

Generally, a living body has high transparency with regard to a light of a wavelength of 700 to 900 nm. A Raman scattering light specific to glucose has a smaller wave number than the irradiation light by approximately 1100 to 1200 cm$^{-1}$. Accordingly, by setting the wavelength of the irradiation light to be 700 to 800 nm, both of the irradiation light and the surface enhanced Raman scattering light can utilize the high transparency described above. Namely, the wavelength of the irradiation light irradiated by the light source 9 is not limited to 785 nm, but can be selected within the range of 700 to 800 nm.

In the embodiment 1, because the circular beam of the linear-polarized light 5 has identical size (diameter: 100 micro meters, for example) to the disk-shaped particle chip 3, the amplitude Am is maximized, thus, S/N is improved.

The equation (V) is generalized into the following equation (VI). That is, in the case where a target chemical substance has Raman shift of B cm$^{-1}$ which is specific to the chemical substance, the center wavelength lambda$_2$ of the filter which is used as the filter 13 is calculated by the following formula (VI).

[math. 6]

$$\lambda_2 = \frac{10^7 \cdot \lambda_1}{10^7 - B \cdot \lambda_1} \text{ (nm)} \tag{VI}$$

B: Raman shift of the biological substance (Embodiment 2)

A method and a device for measuring a concentration of a biological substance according to the embodiment 2 are described below.

Figure 7:
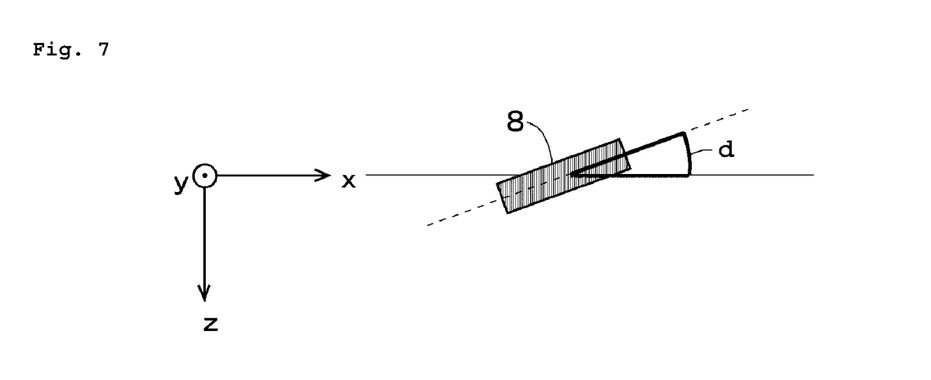
FIG. 7 shows a shift amount d of the particle 8 from the x-direction according to the embodiment 2.
Figure 8:
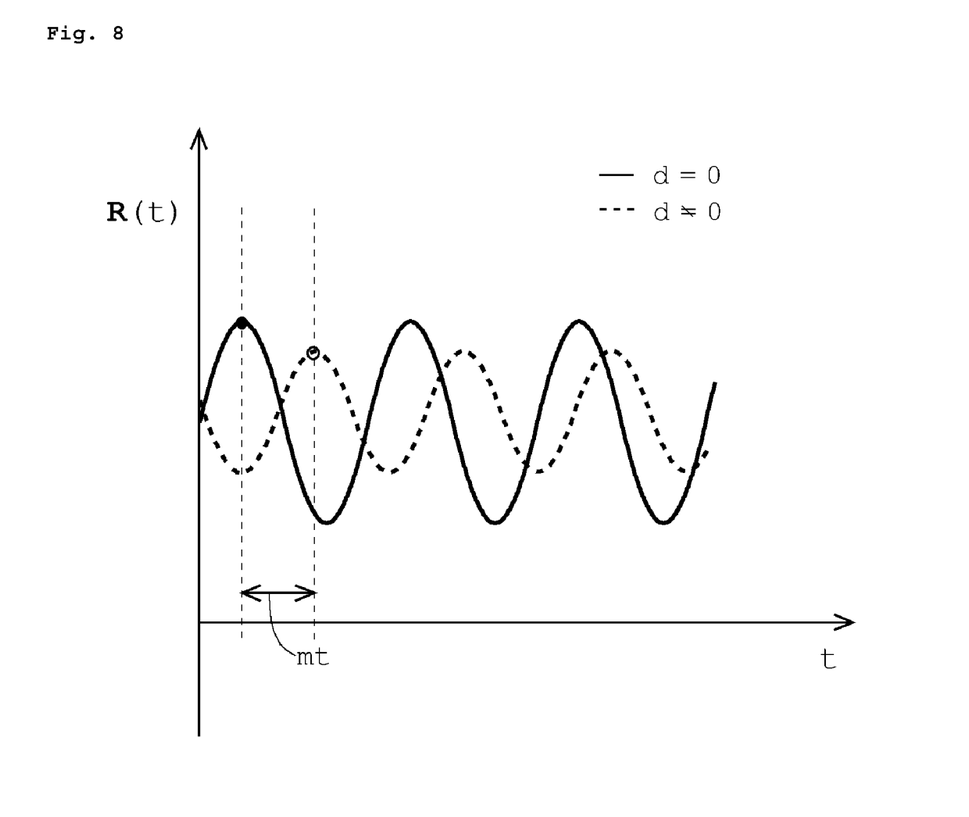
FIG. 8 shows a phase difference of the light receiving signal R(t) according to the embodiment 2.
Figure 9:
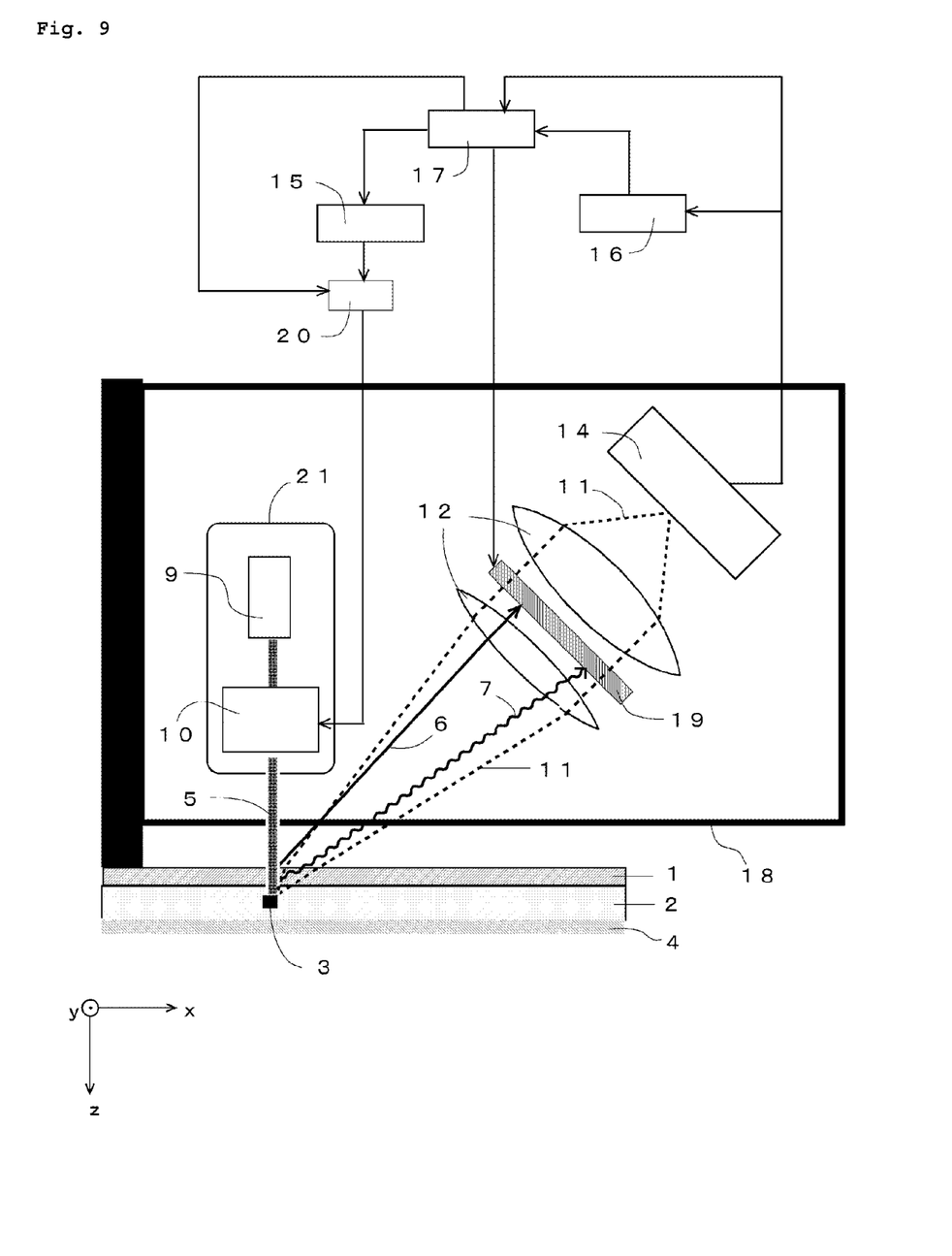
FIG. 9 shows a measuring device according to the embodiment 2.

FIG. 7 shows the longitudinal axis direction of the particle 8. FIG. 8 shows the relationship of the signal R(t) received by the light sensor 14, and a phase of the polarization direction of the linear-polarized light 5. FIG. 9 shows the measuring device according to the embodiment 2. The differences from the embodiment 1 are described below.

A switchable filter 19 can switch the wavelength of the penetrating light to the wavelength of the linear-polarized light 5 or the wavelength of the Raman scattering light specific to the biological substance. When the biological substance is glucose, and the center wavelength of the linear-polarized light 5 is 785 nm, the switchable filter 19 switches the center wavelength of the penetrating light to 785 nm, or 860.7 nm, which is the wavelength of the Raman scattering light specific to glucose.

The computer 17 controls the switchable filter 19 to determine which light penetrate.

A phase shifter 20 shifts the phase of the modulation signal to be transmitted from the signal generator 15 to the polarized modulator 10 on the basis of the instructions by the computer 17. The shift of the phase of the modulation signal allows the phase of the polarization direction of the linear-polarized light 5 to be shifted.

In the embodiment 2, it is assumed that the longitudinal axis direction of the particles 8 has been shifted by d rad from x direction in xy-plane as shown in FIG. 7, due to an error of the position generated on the implantation of the particle chip 3 into the living body, or growth of the living body, and aging of the living body.

As a result of the shift, the longitudinal direction of the particle 8 intersects with x direction. It causes phase difference between the signal R(t) in a case where the x direction and the longitudinal direction are not parallel to one another, and the polarization direction of the linear-polarizedlight 5. The phase difference mt is represented by following equation (VII).

[math. 7]

$$mt = \frac{d}{\omega} \quad \text{(VII)}$$

mt: phase difference between the signal R(t) and porali­zation direction of the linear-polarized light 5

ω: modulation angular frequency of the polarization direction of the linear-polarized light 5 d: magnitude of the angle formed by the x direction and longitudinal direction of the particle 8

When the phase detection is performed with the lock-in amplifier 16, the signal R(t) is maximized on the phase difference mt of 0. Accordingly, the phase of the modulated signal transmitted from the signal generator 15 to the polarization modulator 10 is adjusted to maximize the signal R(t) in such a manner that the phase difference mt is 0.

The intensity of the light scattered by the particle 8 while the localized surface plasmon resonance is generating (hereinafter, resonated Rayleigh scattering light) is maximized at the moment when the polarization direction of the linear-polarized light 5 agree with the longitudinal axis direction of the particles 8, namely the moment in which the magnitude of the angle between the polarized direction and the x direction is equal to the d rad.

Accordingly, in advance of the measurement, the polarization direction of the linear-polarization light 5 is varied, the polarization direction d in which the intensity of the scattering light is maximized is confirmed, while the variation of the intensity of the light scattered by the particles 8 is measured. The confirmation is conducted by observing resonated Rayleigh scattering light. An accuracy of the confirmation is high, because the intensity of the resonated Rayleigh scattering light is extremely higher than that of the surface enhanced Raman scattering light of the biological substances located on the periphery of the particle 8.

Then, on the measurement, the phase of reference signal transmitted from the signal generator 15 to the lock-in amplifier 16 is shifted by −d/omega, and the signal received by the lock-in amplifier 16 is maximized.

Next, a measuring method according to embodiment 2 is described. First, the computer 17 instructs in such a manner that a light with a wavelength of 785 nm penetrates the switchable filter 19. Then, the computer 17 operates the signal generator 15 and the polarization modulator 10 to rotate the polarization direction of the linear-polarized light 5 by 360 degree. The computer memorizes the resulting signal R(t). The polarization direction (namely, d) of the linear-polarized light 5 which maximizes the signal R(t) is determined. The computer 17 set the phase shifted by the phase shifter 20 to −d/omega.

Subsequently, similarly to the embodiment 1, the polarization direction of the linear-polarized light 5 is modulated and the concentration of the biological substance is calculated from the signal received by the lock-in amplifier 16.

In the embodiment 2, the phase difference generated by the shift is compensated for before the concentration of the biological sample is measured. Accordingly, even when the direction of the particle chip 3 varies due to the error of the position on the implantation into the living body, growth of the living body, or aging of the living body, a measurement with high accuracy is maintained.

Industrial Applicability

A method and a device of the present invention for measuring a living component lower the influence of the stray light and the interruption component. Particularly, the present invention is employed to measure a concentration of the biological substance contained in a body fluid using a particle which can generate localized surface plasmon resonance in a living body.

| REFERENCE SIGNS LIST | |
|---|---|
| 1: | epidermal tissue |
| 2: | dermal tissue |
| 3: | particle chip |
| 4: | hypodermal tissue |
| 5: | linear-polarized light |
| 6: | reflected light |
| 7: | diffused light and scattered light |
| 8: | particle having a longitudinal axes |
| 9: | light source |
| 10: | polarized modulator |
| 11: | surface enhanced Raman scattering light |
| 12: | light system |
| 13: | filter |
| 14: | light sensor |
| 15: | signal generator |
| 16: | lock-in amplifier |
| 17: | computer |
| 18: | support |
| 19: | switchable filter |
| 20: | phase shifter |
| 21: | projection module |
| 22: | halogen lamp |
| 23: | lens |
| 24: | filter |
| 25: | light polarizer |

The invention claimed is:

1. A method for measuring a concentration of a biological substance contained in a living body having a particle chip implanted therein, wherein the particle chip includes on the surface thereof, a plurality of particles each of which has a longitudinal axis, the method comprising steps of:

applying a linear-polarized light to the particle chip;

modulating, before the step of applying the linear-polarized light, a polarization direction of the linear-polarized light, in order to cause an angle θ to be periodically varied over time t through rotation of the polarization direction, wherein the angle θ is formed by the polarization direction and a direction x, and the longitudinal axes of the particles are oriented in the direction x;

receiving a surface enhanced Raman scattering light generated from emission on the particle chip of the linear-polarized light that has undergone the rotation of its polarization direction in the step of modulating, to obtain a signal of the surface enhanced Raman scattering light; and calculating the concentration of the biological substance based on a magnitude of the obtained signal in the step of receiving, which varies in response to the periodically varied angle θ.

2. The method according to claim 1, wherein:

the polarization direction is rotated at angular speed ω in the step of modulating, the signal of the received light is represented as R (t) in the following equation (III):

$$R(t) = Am \cdot \sin(\omega t) + D \quad \text{(III)}$$

where D is a constant number, an amplitude Am represents the magnitude of the signal of the received light corresponding to the periodically varied angle θ, and the concentration of the biological substance is obtained on the basis of the amplitude Am for the signal R(t) in the step of calculating.

3. The method according to claim 2, wherein the concentration is obtained through calculation of the amplitude Am and a standard curve.

4. The method according to claim 1, wherein the linear-polarized light has a wavelength $\lambda_1$, the surface enhanced Raman scattering light passes a filter having a central wavelength $\lambda_2$, before being received in the step of receiving, and the wavelength $\lambda_2$ is represented by the following equation (VI):

$$\lambda_2 = \frac{10^7 \cdot \lambda_1}{10^7 - B \cdot \lambda_1} \text{(nm)}, \tag{VI}$$

where B is a Raman shift of the biological substance.

5. The method according to claim 4, wherein a value of the full width at half maximum of the filter is 3 nm.

6. The method according to claim 4, wherein the wavelength $\lambda_1$ is 785 nm and the wavelength $\lambda_2$ is 860.7 nm.

7. An apparatus for measuring a concentration of a biological substance contained in a living body having a particle chip implanted therein, wherein the particle chip includes on the surface thereof, a plurality of particles each of which has a longitudinal axis, the apparatus comprising:
means for emitting a linear-polarized light to the particle chip;
means for modulating, before the emitting of the linear-polarized light, a polarization direction of the linear-polarized light, in order to cause an angle θ to be periodically varied over time t through rotation of the polarization direction, wherein the angle θ is formed by the polarization direction and a direction x, and the longitudinal axes of the particles are oriented in the direction x;
means for receiving a surface enhanced Raman scattering light generated from emission on the particle chip of the linear-polarized light that has undergone the rotation of its polarization direction by the modulating means, to obtain a signal of the surface enhanced Raman scattering light; and
means for calculating the concentration of the biological substance based on a magnitude of the signal obtained by the receiving means, which varies in response to the periodically varied angle θ.

8. The apparatus according to claim 7, wherein:
the polarization direction is rotated at angular speed ω by the modulating means,
the signal of the received light is represented as R (t) in the following equation (III):

$$R(t) = Am \cdot \sin(\omega t) + D \tag{III}$$

where D is a constant number, an amplitude Am represents the magnitude of the signal of the received lights corresponding to the periodically varied angle θ, and
the calculating means calculates the concentration of the biological substance on the basis of the amplitude Am for the signal R (t).

9. The apparatus according to claim 8, wherein the concentration is obtained through calculation of the amplitude Am and a standard curve.

10. The apparatus according to claim 7, wherein the linear-polarized light has a wavelength $\lambda_1$, the surface enhanced Raman scattering light passes a filter having a central wavelength $\lambda_2$, before the receiving means receives it, and the wavelength $\lambda_2$ is represented by the following equation (VI):

$$\lambda_2 = \frac{10^7 \cdot \lambda_1}{10^7 - B \cdot \lambda_1} \text{(nm)}, \tag{VI}$$

where B is Raman shift of the biological substance.

11. The apparatus according to claim 10, wherein a value of the full width at half maximum of the filter is 3 nm.

12. The apparatus according to claim 10, wherein the wavelength $\lambda_1$ is 785 nm and the wavelength $\lambda_2$ is 860.7 nm.

* * * * *